US010683138B2

United States Patent
Cote et al.

(10) Patent No.: US 10,683,138 B2
(45) Date of Patent: Jun. 16, 2020

(54) ERGONOMIC HANDLES FOR CONTAINERS

(71) Applicant: O&M Halyard, Inc., Mechanicsville, VA (US)

(72) Inventors: Anne E. Cote, Milton, GA (US); Travis W. Klyber, Roswell, GA (US); Edward B. Madsen, Cumming, GA (US); Tracy J. White, Cumming, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 0 days.

(21) Appl. No.: 16/158,487

(22) Filed: Oct. 12, 2018

(65) Prior Publication Data

US 2020/0115107 A1    Apr. 16, 2020

(51) Int. Cl.
  *B65D 25/28* (2006.01)
  *A61B 50/30* (2016.01)
  *B62B 5/06* (2006.01)

(52) U.S. Cl.
  CPC .......... *B65D 25/2835* (2013.01); *A61B 50/30* (2016.02); *B62B 5/064* (2013.01); *B65D 2525/288* (2013.01)

(58) Field of Classification Search
  CPC ............ B65D 25/2841; B65D 25/2844; B65D 25/2838; B65D 25/2835; B65D 25/28; A61B 50/30; B62B 5/064; B62B 5/06
  USPC ....... 220/757, 762, 763, 764, 752, 676, 759; 16/430, 425, 422, 110.1
  See application file for complete search history.

(56) References Cited

U.S. PATENT DOCUMENTS

| 4,111,476 A | 9/1978 | Jacobs |
| 4,818,502 A | 4/1989 | Taschner |
| 6,079,590 A * | 6/2000 | Munari ................ A47J 45/061 220/762 |
| 6,116,452 A | 9/2000 | Hamel et al. |
| 6,247,739 B1 | 6/2001 | Lyon |
| 6,725,491 B2 | 4/2004 | Hung |
| 7,726,712 B2 | 6/2010 | DuBois |
| 7,861,860 B2 | 1/2011 | Bettenhausen et al. |
| 8,011,530 B2 * | 9/2011 | Kutsch ................... A47J 45/07 16/110.1 |

(Continued)

FOREIGN PATENT DOCUMENTS

| DE | 102009011528 A1 | 8/2010 |
| DE | 10 2012 102 425 A1 | 9/2013 |

(Continued)

*Primary Examiner* — Robert J Hicks
(74) *Attorney, Agent, or Firm* — Dority & Manning, P.A.

(57) ABSTRACT

Handles for containers and sterilization containers are provided. For example, a handle for a sterilization container comprises a base portion, a grip portion connected to the base portion, and a stop. The base portion is repositionable with respect to the container to change an orientation of the grip portion with respect to a bottom surface of the container. In some embodiments, a sterilization container comprises a body having a bottom surface, a lid, a first handle attached to a first end of the body, and a second handle attached to a second end of the body. Each handle includes a base portion rotatable within a plane parallel to the respective end of the body to reposition the handle with respect to the body, which changes an orientation of a grip portion of each handle with respect to the bottom surface.

20 Claims, 4 Drawing Sheets

(56) References Cited

U.S. PATENT DOCUMENTS

| | | |
|---|---|---|
| 8,608,719 B2 | 12/2013 | Ray |
| 9,051,084 B2 | 6/2015 | Goforth |
| 9,550,510 B2 | 1/2017 | Huguet et al. |
| 2007/0012707 A1 | 1/2007 | Rattay |
| 2017/0158412 A1 | 6/2017 | Seiders et al. |

FOREIGN PATENT DOCUMENTS

| | | |
|---|---|---|
| EP | 2 918 758 A2 | 9/2015 |
| JP | 2004-308175 A | 11/2004 |

* cited by examiner

ERGONOMIC HANDLES FOR CONTAINERS

FIELD

The subject matter of the present disclosure relates generally to handles for containers and, more particularly, to sterilization containers with ergonomic handles for lifting and handling the sterilization containers.

BACKGROUND

Many of the surgical instruments and supplies used in an operating room (OR) are reusable. These instruments and supplies typically include such things as clamps, scalpel blade handles, retractors, forceps, scissors, surgeon's towels, basins, and the like. All of these supplies must be collected after each procedure, decontaminated, placed in a sterilization container, and sterilized before they can be used again in another procedure. The sterilization container or packaging system used must be of the size and shape to accommodate the items to be sterilized and must be compatible with and withstand the physical conditions of the sterilization process. Typical sterilization packages or containers include disposable wraps and reusable rigid containers (RCs), which include a lid, a body, a filter, and one or more sealing gaskets. Typical means of sterilizing instruments include, among others, autoclaving with steam, exposure to ethylene oxide gas, and exposure to hydrogen peroxide plasma, as is done with the STERRAD® Sterilization System from Advanced Sterilization Products, Irvine, Calif. After the package and its contents have been sterilized, the sterilization package typically is stored until it is needed for a surgical procedure.

Preventing postoperative infection is critically important in surgical procedures. The use of properly sterilized surgical instruments is a key piece of the infection prevention paradigm. Sterilization package or container systems are designed to allow for proper steam penetration, post-autoclave cooling, indefinite aseptic storage of the instruments, and aseptic opening and removal of the instruments. RCs exhibit good durability and due to their reusability, represent a very economical sterilization method. However, RCs can be heavy, cumbersome, and/or awkward for a user to handle, depending, e.g., on the container's dimensions and weight relative to the user's size and physical abilities. Of course, such problems are also common to other types of containers, such as storage boxes, bins, or the like over a certain size. Often, the handles on rigid sterilization containers and other containers are not in a position or orientation for the most efficient, comfortable, and/or safe handling of the container.

Consequently, there is a need for a handle that overcomes the shortcomings of known container handles. In particular, a repositionable handle would be desirable. More particularly, a handle having a grip portion that may be changed from one orientation to another such that the grip portion has two or more orientations would be beneficial. Further, a handle changeable between two or more positions and having features for securing the handle in a particular position without compromising the ability to subsequently change the position of the handle would be advantageous. Additionally, a sterilization container for containing articles for sterilization having repositionable handles would be useful.

SUMMARY

The present invention provides handles for containers, such as sterilization containers, that are changeable between two or more positions to provide a more ergonomic grip for a user. Additional aspects and advantages of the invention will be set forth in part in the following description, may be apparent from the description, or may be learned through practice of the invention.

In one aspect, the present subject matter is directed to a handle for a sterilization container. The handle comprises a base portion, a grip portion connected to the base portion, and a stop. The base portion is repositionable with respect to the sterilization container to change an orientation of the grip portion with respect to a bottom surface of the sterilization container.

In another aspect, the present subject matter is directed to a sterilization container. The sterilization container comprises a body having an open top portion and an opposite bottom surface, a lid for covering the open top portion of the body to close the sterilization container, and a pair of handles. The body and the lid together define an interior of the sterilization container. A first handle of the pair of handles is attached to a first end of the body, and a second handle of the pair of handles is attached to a second end of the body. Each of the first and second handles is repositionable with respect to the body. A base portion of the first handle is rotatable within a plane parallel to the first end of the body to reposition the first handle with respect to the body. Similarly, a base portion of the second handle is rotatable within a plane parallel to the second end of the body to reposition the second handle with respect to the body. Repositioning each of the first handle and second handle with respect to the body changes an orientation of a grip portion of each of the first handle and second handle with respect to the bottom surface of the body.

In still another aspect, the present subject matter is directed to a sterilization container comprising a body having an open top portion and an opposite bottom surface. The sterilization container further comprises a lid for covering the open top portion of the body to close the sterilization container. The body and the lid together define an interior of the sterilization container. The sterilization container also comprises a first handle attached to a first end of the body and a second handle attached to a second end of the body. The first handle includes a first base portion rotatable within a plane parallel to the first end of the body to reposition the first handle with respect to the body, a first grip portion, and a first stop that engages a first mounting plate attached to the first end to hold the first base portion in position with respect to the first end. The second handle includes a second base portion rotatable within a plane parallel to the second end of the body to reposition the second handle with respect to the body, a second grip portion, and a second stop that engages a second mounting plate attached to the second end to hold the second base portion in position with respect to the second end. Repositioning the first handle with respect to the first end changes an orientation of the first grip portion with respect to the bottom surface of the body. Further, repositioning the second handle with respect to the second end changes an orientation of the second grip portion with respect to the bottom surface of the body.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Described herein are sterilization containers and components thereof suitable for use in a variety of procedures for containing, sterilizing, storing, and using sterilized items such as surgical supplies. While described in conjunction with its use in hospital and surgical room procedures, the present subject matter is intended for use wherever there is a need for sterilized materials. Consequently, the following description should not be considered a limitation as to the scope of use of the present subject matter.

Generally, the present subject matter provides handles used for lifting a container that can change positions, for example, to make the container easier for a particular user to lift (e.g., one orientation of the handles may be more ergonomic for a shorter person while a different orientation is more ergonomic for a taller person) and/or to make the container easier for a user to lift to a particular location (e.g., overhead). For instance, the handles may have two or more different orientations with respect to a bottom surface of the container and include features for repositioning the handles from orientation to another. As an example, each handle of a pair of handles secured to a container may be changeable from a horizontal position (parallel or 0° relative to the bottom surface of the container), to a 45° position or orientation relative to the bottom surface, and to a vertical position (perpendicular or 90° relative to the bottom surface). Thus, the handles are not fixed in a particular position such that the orientation of the handles is unchangeable; however, the handles also include features for securing the handles in a particular position such that a user may grip the handles without the handles moving to a different position, although the handles are repositionable when they are unsecured from the particular position. In particular embodiments, the container is a sterilization container for sterilizing, e.g., surgical instruments and/or supplies.

Figure 1:
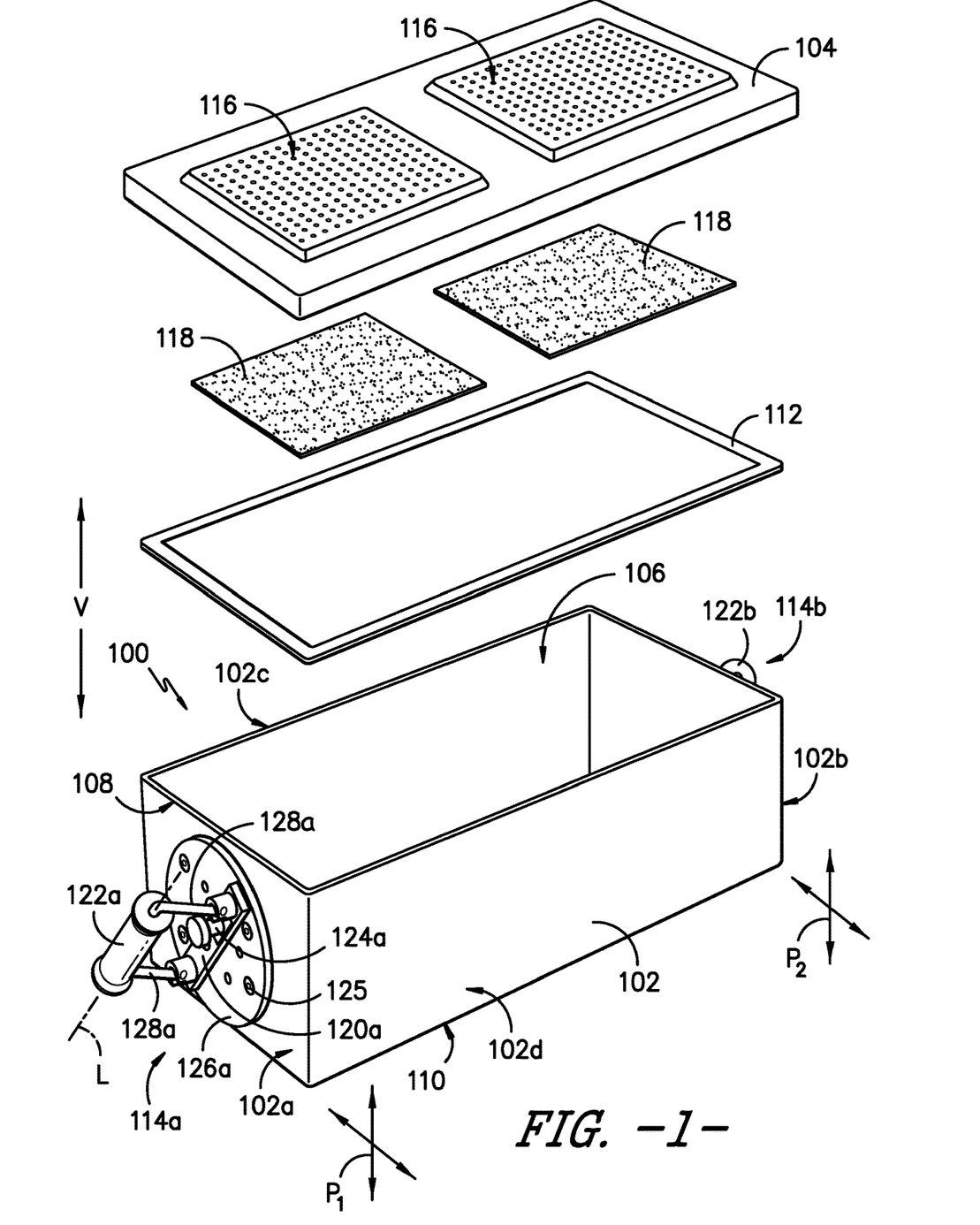
FIG. 1 provides an exploded perspective view of a sterilization container having a pair of ergonomic handles, according to an exemplary embodiment of the present subject matter.
Figure 2:
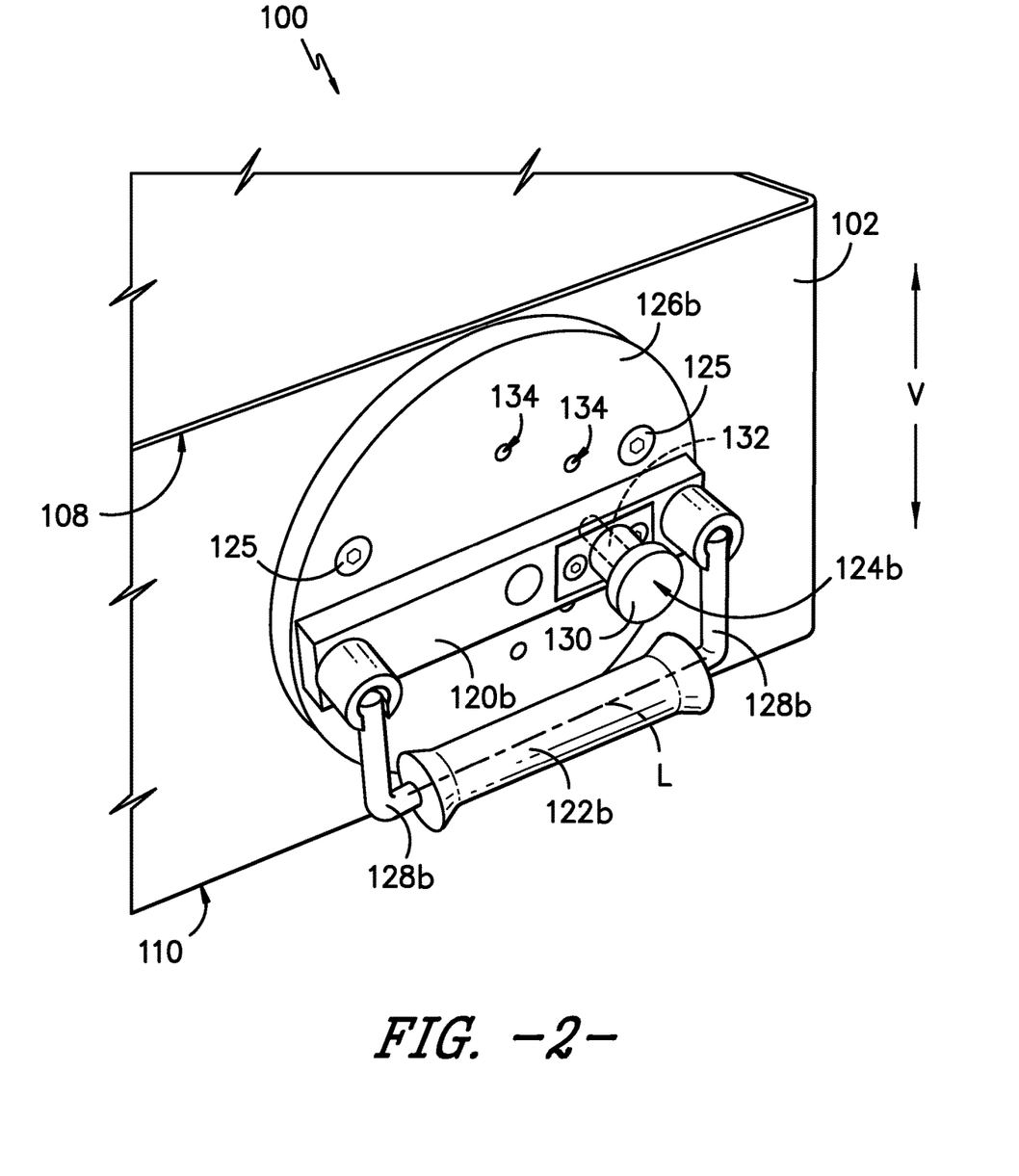
FIG. 2 provides an end perspective view of the sterilization container of FIG. 1 and one handle of the pair of handles, where the handle is in a first orientation with respect to a bottom surface of the sterilization container.

FIG. 1 provides a perspective view of a sterilization container 100 comprising a body 102 and a cover or lid 104, according to an exemplary embodiment of the present subject matter. The body 102 and lid 104 together define an interior 106 of the sterilization container 100. One or more articles, e.g., clamps, scalpel blade handles, retractors, forceps, scissors, surgeon's towels, basins, and like surgical devices, instruments, or supplies, may be placed in the interior 106 of the container 100 for sterilization such that the article(s) may be reused in another procedure.

The body 102 of the sterilization container 100 includes an open top portion 108 and a bottom surface 110 opposite the open top portion 108 along a vertical direction V. It will be appreciated that the lid 104 may be attached or secured to the body 102 such that the lid 104 covers the open top portion 108 of the body 102 to close the container 100. Moreover, a gasket 112 is compressed between the lid 104 and body 102 to seal the container 100 against an ingress of contaminants. The lid 104 may be retained on the body 102 by one or more latch assemblies (not shown), and the one or more latch assemblies also may apply a force to the lid 104 to compress the gasket 112 between the lid 104 and body 102. In some embodiments, the gasket 112 extends within a groove defined in the body 102, or in other embodiments, the gasket 112 extends within a groove define in the lid 104. In still other embodiments, the gasket 112 is not retained in a portion of the body 102 or lid 104 but is positioned between the lid 104 and body 102 as the container 100 is assembled.

As further shown in FIG. 1, the container 100 includes a pair of handles 114 for lifting, carrying, or otherwise handling the container 100. A first handle 114a is attached to a first end 102a of the body 102, and a second handle 114b is attached to a second end 102b of the body 102, where the second end 102b is opposite the first end 102a. In other embodiments, the first handle 114a may be attached to a first side 102c of the body 102, and the second handle 114b may be attached to a second side 102d of the body 102, where the second side 102d is opposite the first side 102c and the first and second sides 102c, 102d extend between the first and second ends 102a, 102b. However, the sterilization container 100 need not have a generally rectangular shape as shown in FIG. 1, but the container 100 may have any appropriate shape for containing items to be sterilized. Additionally, other configurations, placements, and/or numbers of the handles 114 may be used. Further, although a particular figure may illustrate only one handle 114, it will be appreciated that any other handles 114 of the container 100 may be configured the same as or identical to the illustrated handle 114. The handles 114 are described in greater detail herein.

Moreover, as illustrated in FIG. 1, the lid 104 defines one or more vents 116 therein. The vent(s) 116 permit fluids and gases, such as air, steam, and chemical sterilization agents or sterilants, to pass through the lid 104 and into the interior 106 of the sterilization container 100. Further, the vent(s) permit fluids and gases to pass from the interior 106 to the environment external to the container 100, e.g., water vapor may pass through the vent(s) 116 from the container interior 106 during an evaporation phase of a sterilization process after steam is applied to the container 100.

In addition, a filter 118 is positioned within the sterilization container 100 adjacent the vent(s) 116. The filter 118 may be a sheet of material that extends over the open end of the body 102 such that the filter 118 is positioned between the lid 104 and the container interior 106. In other embodiments, a filter 118 may be positioned adjacent each vent 116 in the lid 104, such that the container 100 includes a filter 118 for each vent 116 as shown in FIG. 1, rather than a single filter 118 that extends across the entire open top portion 108 of the body 102 such that the single filter 118 is adjacent all of the vents 116 in the lid 104 (whether the lid 104 defines one or a plurality of vents 116). As shown in FIG. 1, each filter 118 may be configured as a sheet of material. However, the filter(s) 118 need not be configured as a sheet but may have any suitable configuration or construction. The filter(s) 118 can be made from a number of materials and, generally, may be made of a material from one of two main classes, reusables and disposables. Reusables are materials that, as the name suggests, can be reused, typically by washing or some other form of cleaning. Disposables, on the other hand, usually are one-use items that are discarded or recycled after their initial use. Generally, cloth, linen, or other woven materials fall into the reusable category while disposables normally include nonwoven materials made from either or both natural and synthetic fibers such as paper, fibrous polymeric nonwovens, and films, which are capable of passing sterilants and retarding transmission of bacteria and other contaminants.

Nonwoven sterilization materials present several advantages due to their barrier properties, economics, and consistent quality. The nonwoven materials can be made from a variety of processes including, but not limited to, air laying processes, wet laid processes, hydroentangling processes, spunbonding, meltblowing, staple fiber carding and bonding, and solution spinning. The fibers themselves can be made from a variety of both natural and synthetic materials including, but not limited to, cellulose, rayon, nylon, polyesters, polyolefins, and many other materials. The fibers may be relatively short, staple length fibers, typically less than three inches, or longer and substantially more continuous fibers such as are produced by spunbonding and meltblowing processes. Whatever materials are chosen, the resultant material for the filter(s) 118 must be compatible with the particular sterilization technique being used and must also provide both strength and barrier properties to maintain the sterile nature of the contents of the sterilization container 100 until use.

In some embodiments, the lid 104 may define one or more windows through which the filter(s) 118 are visible to a user of the container 100, and the filter material may be a transparent breathable film such that the user can see through the filter(s) 118 and into the interior 106 of the container 100. However, in other embodiments, the filter(s) 118 may be made from a translucent or opaque material, such as, e.g., a translucent breathable film, a SMS material, or the like. For example, polyolefin-based fibers and their resultant nonwovens are particularly well-suited for the production of a flexible filter 118, and a polypropylene spunbonded nonwoven can be used to impart strength characteristics to the filter 118. In some embodiments, the filter(s) 118 may be made from laminates such as a laminate of spunbonded and meltblown or spunbonded, meltblown, spunbonded to impart both strength and barrier properties to the filter(s) 118. A spunbonded-meltblown-spunbonded (SMS) material is made from three separate layers that are laminated to one another. The method of making these layers is known and described in U.S. Pat. No. 4,041,203 to Brock, et al., which is incorporated herein in its entirety by reference. The material of Brock, et al. is a three layer laminate of spunbonded-meltblown-spunbonded layers. The two outer layers of SMS are a spunbonded material made from extruded polyolefin fibers, or filaments, laid down in a random pattern and then bonded to one another. The inner layer is a meltblown layer also made from extruded polyolefin fibers generally of a smaller diameter than the fibers in the spunbonded layers. As a result, the meltblown layer provides increased barrier properties due to its fine fiber structure, which permits the sterilizing agent to pass through the fabric while preventing passage of bacteria and other contaminants. Conversely, the two outer spunbonded layers provide a greater portion of the strength factor in the overall laminate. The laminate may be prepared using an intermittent bond pattern that is preferably employed with the pattern being substantially regularly repeating over the surface of the laminate. The pattern is selected such that the bonds may occupy about 5% to about 50% of the surface area of the laminate. Desirably, the bonds may occupy about 10% to about 30% of the surface area of the laminate. In an exemplary embodiment, each filter 118 is made from a SMS material, but the filter(s) 118 also may be made from other suitable materials.

Referring to FIG. 1, the handles 114 described herein are repositionable and, thus, may be referred to as ergonomic handles 114 because the handles 114 can be moved from one position to another to make it easier, safer, and/or more comfortable for a user to lift and/or carry the sterilization container 100. More particularly, each handle 114 comprises a base portion 120, a grip portion 122, a stop 124, and a mounting plate 126. That is, the first handle 114a includes first base portion 120a, first grip portion 122a, first stop 124a, and first mounting plate 126a, and the second handle 114b includes second base portion 120b, second grip portion 122b, second stop 124b, and second mounting plate 126b. The mounting plate 126 of each handle 114 is attached or secured to the container body 102, e.g., using one or more fasteners 125 in a manner that prevents an ingress of contaminants to the interior 106 of the container 100. The base portion 120 of each handle 114 is repositionable with respect to the sterilization container 100 to change an orientation of the grip portion 122 with respect to the bottom surface 110 of the container 100.

Figure 3:
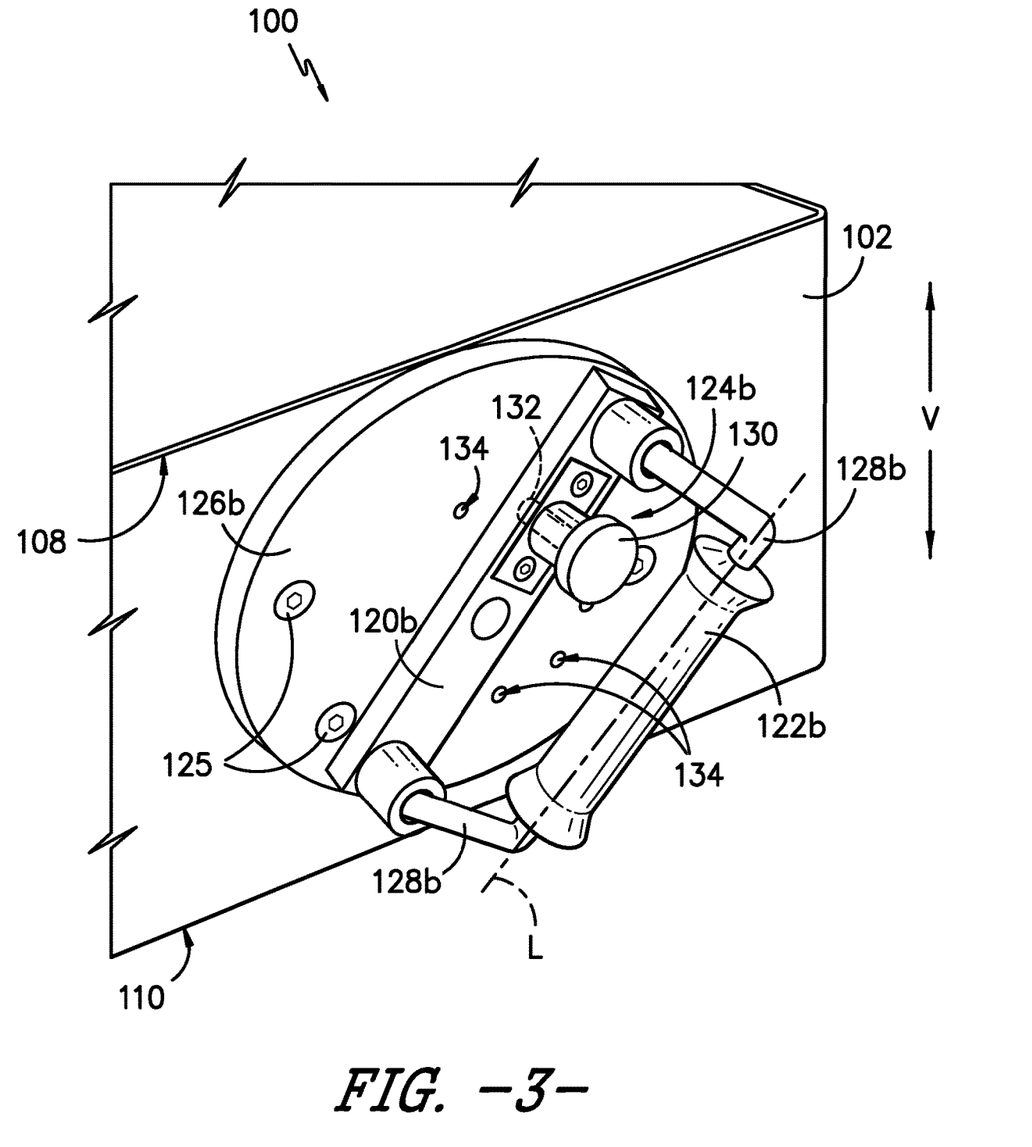
FIG. 3 provides the end perspective view of FIG. 2 with the handle in a second orientation with respect to the bottom surface of the sterilization container.
Figure 4:
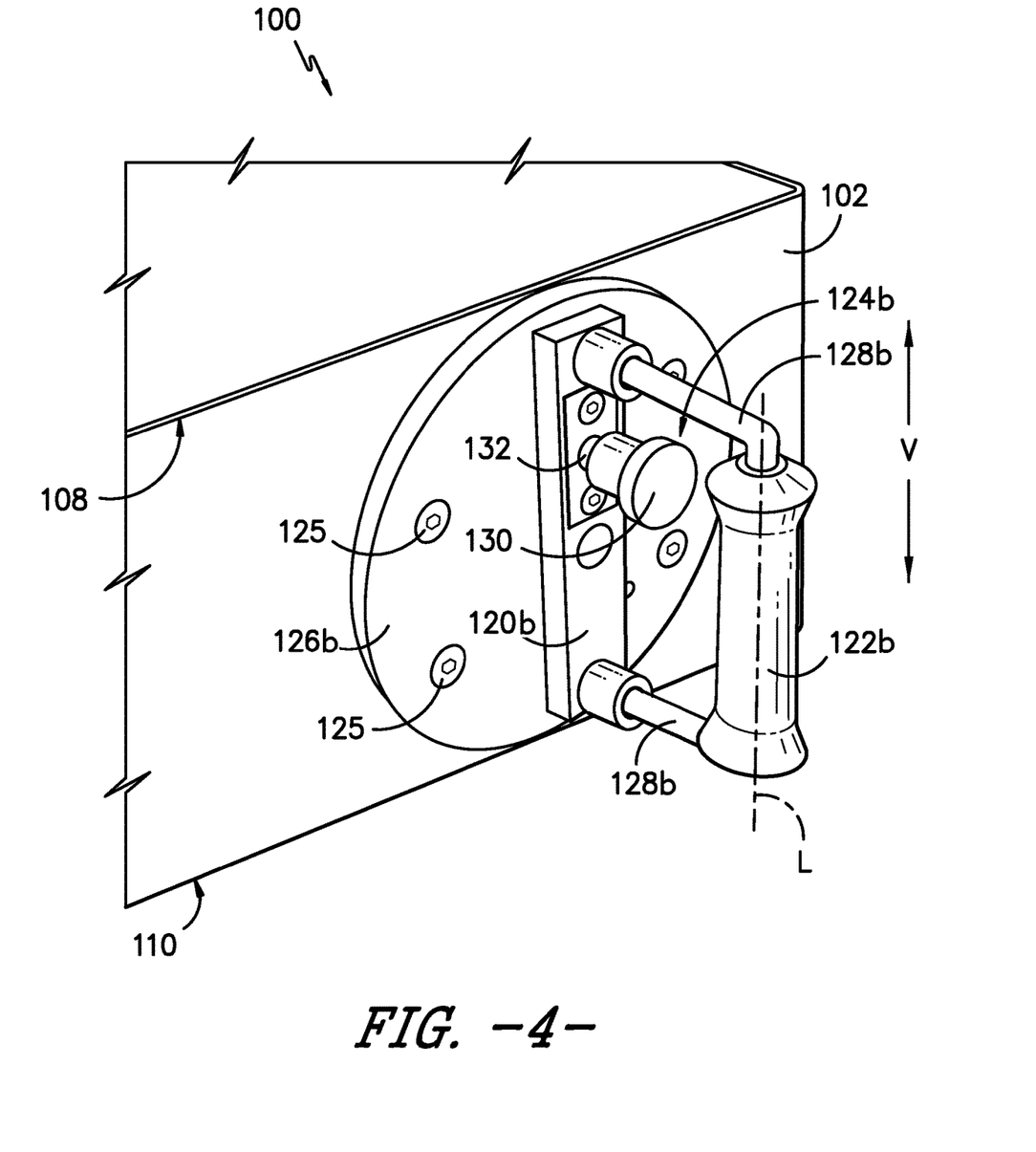
FIG. 4 provides the end perspective view of FIG. 2 with the handle in a third orientation with respect to the bottom surface of the sterilization container.

As illustrated in FIGS. 1-4, the grip portion 122 of each handle 114 extends along a line L. The orientation of the grip portion 122 may include any orientation from 0° to 180°, measured as the angle between the line L and the bottom surface 110 of the container 100. For example, referring to FIG. 2, the orientation of the grip portion 122 includes a first orientation in which the line L is parallel to the bottom surface 110, i.e., the angle between the line L and the bottom surface 110 is 0°. As shown in FIG. 3, the depicted exemplary embodiment of the grip portion 122 also includes a second orientation in which the line L is at an angle of approximately 45° with respect to the bottom surface 110. In various embodiments, the grip portion 122 in the second orientation may be at an angle between approximately 30° and approximately 60° with respect to the bottom surface 110. Referring to FIG. 4, the grip portion 122 of the exemplary handle 114 also has a third orientation in which the line L is perpendicular, i.e., at an angle of 90°, to the bottom surface 110. Further, in some embodiments, the grip portion 122 may be repositionable to a plurality of orientations with respect to the bottom surface 110 between 0° and 90° or 0° and 180°. For example, the handle 114 may be repositionable such that the grip portion 122 may be oriented at each of about 30°, about 45°, and about 60° with respect to the bottom surface 110, i.e., the selectable orientations for grip portion 122 include about 30°, about 45°, and about 60°, where the handle may be secured such that the grip portion 122 is retained in the selected orientation a user to lift, carry, or otherwise handle the container 100. Additional or alternative orientations for grip portion 122 may be used as well. Moreover, it will be appreciated that, if the grip portion 122 is at an angle of 180° with respect to the bottom surface 110, the grip portion 122 is essentially in the same orientation as in the first or 0° orientation shown in FIG. 2, i.e., the grip portion 122 would be upside-down compared to the first orientation but the line L would be parallel to the bottom surface 110.

In the exemplary embodiment shown in FIGS. 1-4, the base portion 120 of each handle 114 is rotatable to vary the position of the handle 114 and, thereby, vary the orientation of the grip portion 122. More particularly, the mounting plate 126a of the first handle 114a is attached to the first end 102a of the container body 102, and the base portion 120a of the first handle 114a is secured to the first mounting plate 126a such that the first base portion 120a is rotatable within a plane $P_1$ parallel to the first end 102a. A pair of first arms 128a, each arm 128a having a length $l_{first}$, connects the first grip portion 122a to the first base portion 120a. Thus, when the first base portion 120a rotates, the first grip portion 122a connected to the base portion 120a by the first arms 128a also rotates, thereby changing the orientation of the grip portion 122a. Further, each arm 128a of the pair of first arms 128a pivots with respect to the first base portion 120a such that the first grip portion 122a has a non-extended position in which the grip portion 122a is adjacent to the base portion 120a and an extended position in which the grip portion 122a is spaced apart from the base portion 120a by the length $l_{first}$ of each arm 128a. As such, the grip portion 122a of the first handle 114a may be selectively extended away from the base portion 120a, e.g., to allow a user to fit his or her hand around the grip portion 120a, or may rest against or near the base portion 120a, e.g., to reduce the length of the sterilization container 100. Further, it will be appreciated that the pair of first arms 128a may be two portions of a single piece component that extends through the first grip portion 122a, i.e., each first arm 128a may be a separate piece connected to the first grip portion 122a or may be portions of a single piece that passes through the first grip portion 122a.

Similarly, the mounting plate 126b of the second handle 114b is attached to the second end 102b of the container body 102, and the base portion 120b of the second handle 114b is secured to the second mounting plate 126 such that the second base portion 120b is rotatable within a plane $P_2$ parallel to the second end 102b. A pair of second arms 128b, each arm 128b having a length $l_{second}$, connects the second grip portion 122b to the second base portion 120b. As a result, when the second base portion 120b rotates, the second grip portion 122b connected to the base portion 120b by the second arms 128b also rotates, thereby changing the orientation of the grip portion 122b. Further, like the first arms 128a, each arm 128b of the pair of second arms 128b pivots with respect to the second base portion 120b such that the second grip portion 122b has a non-extended position in which the grip portion 122b is adjacent to the base portion 120b and an extended position in which the grip portion 122b is spaced apart from the base portion 120b by the length $l_{second}$ of each arm 128b. Thus, the grip portion 122b of the second handle 114b may be selectively extended away from the base portion 120b, e.g., to allow a user to fit his or her hand around the grip portion 120b, or may rest against or near the base portion 120b, e.g., to reduce the length of the sterilization container 100. Additionally, it will be appreciated that the pair of second arms 128b may be two portions of a single piece component that extends through the second grip portion 122b, i.e., each second arm 128b may be a separate piece connected to the second grip portion 122b or may be portions of a single piece that passes through the second grip portion 122b.

As further illustrated in FIGS. 1-4, each handle 114 includes a stop 124 for holding the base portion 120 in position with respect to the sterilization container 100. That is, the stop 124 prevents the base portion 120 from rotating with respect to the container 100 such that the grip portion 122 is locked, secured, or held in a particular orientation. The stop 124 engages the mounting plate 126, which is attached or secured to the container 100, to hold the base portion 120 in position with respect to the container 100. More particularly, the stop 124 is moveable between a first position in which the stop 124 engages the mounting plate 126 and a second position in which the stop 124 is disengaged from the mounting plate 126 such that, e.g., the base portion 120 can rotate and thereby be repositioned to alter the orientation of the grip portion 122. For instance, each stop 124 may include a knob 130 that the user may pull to release a plunger 132 from a catch 134, such as a depression, opening, or the like in the mounting plate 126. Thus, in the first position of the stop 124, the plunger 132 engages the catch 134 to prevent the base portion 120 of the handle 114 from rotating. As shown in FIGS. 1-4, a plurality of catches 134 are defined in the mounting plate 126, and each catch 134 corresponds to an orientation of the grip portion 122. That is, the knob 130 and plunger 132 are carried by the base portion 120 such that when the plunger 132 engages a catch 134 of the plurality of catches 134, the grip portion 122 is oriented in a selected orientation, i.e., with the line L of the grip portion 122 at a particular angle with respect to the bottom surface 110 of the container 100. In the second position of the stop 124, i.e., when the user pulls the knob 130 away from the base portion 120, the plunger 132 is released from the catch 134 and the base portion 120 is free to rotate. Of course, the stop 124 may have other configurations as well, and it will be appreciated that each handle 114 includes a suitable feature such as stop 124 to hold the handle 114 in each of the positions the handle 114 may assume.

Thus, in exemplary embodiments, a sterilization container 100 comprises a body 102 that has an open top portion 108 and a bottom surface 110 opposite the open top portion 108. A lid 104 is provided for covering the open top portion 108 of the body 102 to close the sterilization container 100, and the body 102 and the lid 104 together define an interior 106 of the container 100. The container 100 further comprises a pair of handles 114, including a first handle 114a attached to a first end 102a of the container body 102 and a second handle 114b attached to a second end 102b of the container body 102. The first handle 114a includes a first base portion 120a that is rotatable within a plane $P_1$ parallel to the first end 102a to reposition the first handle 114a with respect to the body 102. The first handle 114a also includes a first grip portion 122a and a first stop 124a that engages a first mounting plate 126a attached to the first end 102a to hold the first base portion 120a in position with respect to the first end 102. The second handle 114b includes a second base portion 120b that is rotatable within a plane $P_2$ parallel to the second end 102b to reposition the second handle 114b with respect to the body 102. The second handle 114b also includes a second grip portion 122b and a second stop 124b that engages a second mounting plate 126b attached to the second end 102b to hold the second base portion 120b in position with respect to the second end 102b. As described herein, repositioning the first handle 114a with respect to the first end 102a of the body 102 changes an orientation of the first grip portion 122a with respect to the bottom surface 110 of the body 102, and repositioning the second handle 114b with respect to the second end 102b of the body 102 changes an orientation of the second grip portion 122b with respect to the bottom surface 110. Further, although in the exemplary embodiments described herein the container is a sterilization container, it will be appreciated that the handles 114 described herein may be used with other types of containers, i.e., the present subject matter is not limited to use with sterilization containers but may be applied to any suitable container.

Accordingly, the present subject matter provides handles for containers, such as sterilization containers that contain medical instruments and/or supplies for sterilization such that the instruments and/or supplies can be reused, that are repositionable to change an orientation of the grip portion of each handle with respect to the bottom surface of the container. In exemplary embodiments, each handle includes a base portion that is secured to the container such that the base portion is rotatable with respect to the container to change the orientation of the grip portion, which is attached to the base portion. As an example, the grip portion may be changeable between positions in which the grip portion is oriented parallel to the bottom surface of the container, at an angle between 30° and 60° with respect to the bottom surface (e.g., at a 45° angle with respect to the bottom surface), or perpendicular to the bottom surface.

The repositionable handles improve the ergonomics of the container and, thus, may be referred to as ergonomic handles. More particularly, because the handles are changeable between two or more positions, a user may select a handle position that makes it easier, more comfortable, and/or safer to lift and/or carry the container. Each user that handles the container may select a different position such that the grip portion orientation may depend on the user's height, body type, ability to lift the container chest-high or overhead, etc. On the other hand, a particular user may select a different handle position depending on the type of motion the user expects to perform in handling the container, e.g., the user may position the grip portion of each handle in one orientation to lift the container overhead and may position the grip portion of each handle in a different orientation to carry the container over a certain distance or in a certain environment. Of course, the repositionable handles described herein may have other benefits and advantages as well.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A sterilization container, comprising:
    a body having
        an open top portion and an opposite bottom surface,
        a first side and a second side, and
        a first end and a second end, the first end extending vertically between the open top portion and the bottom surface and horizontally between the first side and the second side; and
    a handle comprising
        a mounting plate attached to the first end of the body,
        a base portion secured to the mounting plate such that the base portion is rotatable within a plane parallel to the first end of the body to change an orientation of the base portion with respect to the bottom surface,
        a grip portion connected to the base portion, and
        a stop for holding the base portion in position with respect to the body,
    wherein the base portion is rotatable with respect to the body to change an orientation of the grip portion with respect to the bottom surface.

2. The sterilization container of claim 1, wherein the grip portion extends along a line, and
    wherein the orientation of the grip portion includes a first orientation in which the line is parallel to the bottom surface, a second orientation in which the line is at an angle between 30° and 60° with respect to the bottom surface, and a third orientation in which the line is perpendicular to the bottom surface.

3. The sterilization container of claim 2, wherein the angle of the second orientation is approximately 45° with respect to the bottom surface.

4. The sterilization container of claim 1, wherein the stop engages the mounting plate to hold the base portion in position with respect to the sterilization container.

5. The sterilization container of claim 4, wherein the stop is moveable between a first position in which the stop engages the mounting plate and a second position in which the stop is disengaged from the mounting plate for repositioning the base portion.

6. The sterilization container of claim 1, wherein a pair of arms connects the grip portion to the base portion, each arm having a length.

7. The sterilization container of claim 6, wherein each arm of the pair of arms pivots with respect to the base portion such that the grip portion has a non-extended position in which the grip portion is adjacent to the base portion and an extended position in which the grip portion is spaced apart from the base portion by the length of each arm.

8. The sterilization container of claim 1, further comprising:
    a lid for covering the open top portion of the body to close the sterilization container, the body and the lid together defining an interior of the sterilization container; and
    a gasket for sealing the interior against an ingress of contaminants.

9. The sterilization container of claim 8, further comprising:
    a second handle comprising
        a second mounting plate attached to the second end of the body,
        a second base portion secured to the second mounting plate such that the second base portion is rotatable within a plane parallel to the second end of the body to change an orientation of the second base portion with respect to the bottom surface,
        a second grip portion connected to the second base portion, and
        a second stop for holding the second base portion in position with respect to the body, wherein the second base portion is rotatable with respect to the body to change an orientation of the second grip portion with respect to the bottom surface.

10. The sterilization container of claim 9, wherein a pair of second arms connects the second grip portion to the second base portion, each second arm having a length.

11. The sterilization container of claim 10, wherein each second arm of the pair of second arms pivots with respect to the second base portion such that the second grip portion has a non-extended position in which the second grip portion is adjacent to the second base portion and an extended position in which the second grip portion is spaced apart from the second base portion by the length of each second arm.

12. The sterilization container of claim 1, wherein the grip portion extends parallel to the base portion and to the first side of the body.

13. The sterilization container of claim 1, wherein the stop comprises a knob and a plunger carried by the base portion, and wherein a plurality of catches are defined in the mounting plate, each catch of the plurality of catches configured to receive the plunger.

14. The sterilization container of claim 13, where the plurality of catches are defined along the mounting plate in an arc shape.

15. The sterilization container of claim 14, wherein an uppermost catch is defined closer to the open top portion than the bottom surface along a vertical direction, and wherein a bottommost catch is defined closer to the bottom surface than the open top portion along the vertical direction.

16. A sterilization container, comprising:
a body having
an open top portion and an opposite bottom surface, and
a first end and an opposite second end;
a lid for covering the open top portion of the body to close the sterilization container, the body and the lid together defining an interior of the sterilization container; and
a pair of handles, a first handle of the pair of handles attached to the first end of the body and comprising a first grip portion, a second handle of the pair of handles attached to the second end of the body and comprising a second grip portion, each of the first and second handles being repositionable with respect to the body,
wherein a base portion of the first handle is rotatable within a first plane parallel to the first end of the body to reposition the first handle with respect to the body,
wherein a base portion of the second handle is rotatable within a second plane parallel to the second end of the body to reposition the second handle with respect to the body,
wherein repositioning the first handle with respect to the body changes an orientation of the first grip portion within the first plane and with respect to the bottom surface of the body, and
wherein repositioning the second handle with respect to the body changes an orientation of the second grip portion within the second plane and with respect to the bottom surface of the body.

17. The sterilization container of claim 16, wherein the orientation of the grip portion of each of the first handle and second handle includes a first orientation that is parallel to the bottom surface, a second orientation that is at an angle between 30° and 60° with respect to the bottom surface, and a third orientation that is perpendicular to the bottom surface.

18. The sterilization container of claim 17, wherein the angle of the second orientation is approximately 45° with respect to the bottom surface.

19. The sterilization container of claim 16, further comprising:
a first stop for holding the base portion of the first handle in position with respect to the first end of the body; and
a second stop for holding the base portion of the second handle in position with respect to the second end of the body.

20. A sterilization container, comprising:
a body having an open top portion and an opposite bottom surface:
a lid for covering the open top portion of the body to close the sterilization container, the body and the lid together defining an interior of the sterilization container; and
a first handle attached to a first end of the body, the first handle including
a first mounting plate attached to the first end,
a first base portion rotatable within a plane parallel to the first end of the body to reposition the first handle with respect to the body,
a first grip portion, and
a first plunger carried by the first base portion that engages one catch of a plurality of catches defined in the first mounting plate to hold the first base portion in position with respect to the first end; and
a second handle attached to a second end of the body, the second handle including
a second mounting plate attached to the second end,
a second base portion rotatable within a plane parallel to the second end of the body to reposition the second handle with respect to the body,
a second grip portion, and
a second plunger carried by the second base portion that engages one catch of a plurality of catches defined in the second mounting plate to hold the second base portion in position with respect to the second end,
wherein repositioning the first handle with respect to the first end changes an orientation of the first grip portion with respect to the bottom surface of the body, and
wherein repositioning the second handle with respect to the second end changes an orientation of the second grip portion with respect to the bottom surface of the body.

* * * * *